(12) United States Patent
Cachia et al.

(10) Patent No.: US 6,632,224 B2
(45) Date of Patent: Oct. 14, 2003

(54) BONE FIXATION SYSTEM

(75) Inventors: Victor V. Cachia, San Juan Capistrano, CA (US); Gerard von Hoffmann, Coto de Caza, CA (US); Brad S. Culbert, Rancho Santa Margarita, CA (US)

(73) Assignee: Triage Medical, Inc., Irvine, CA (US)

( * ) Notice: Subject to any disclaimer, the term of this patent is extended or adjusted under 35 U.S.C. 154(b) by 116 days.

(21) Appl. No.: 09/815,263

(22) Filed: Mar. 22, 2001

(65) Prior Publication Data

US 2001/0049529 A1 Dec. 6, 2001

Related U.S. Application Data

(60) Continuation-in-part of application No. 09/558,057, filed on Apr. 26, 2000, now abandoned, which is a continuation-in-part of application No. 09/266,138, filed on Mar. 10, 1999, now abandoned, which is a division of application No. 08/745,652, filed on Nov. 12, 1996, now Pat. No. 5,893,850.

(51) Int. Cl.7 .............................................. A61B 17/56
(52) U.S. Cl. ....................................................... 606/72
(58) Field of Search ............................. 606/53, 60, 63, 606/68, 72, 75; 411/43, 450, 34, 35, 37, 38, 46, 48

(56) References Cited

U.S. PATENT DOCUMENTS

| | | | |
|---|---|---|---|
| 2,077,804 A | | 4/1937 | Morrison |
| 2,485,531 A | | 10/1949 | Dzus et al. |
| 2,489,870 A | | 11/1949 | Dzus |
| 3,489,143 A | | 1/1970 | Holloran |
| 4,052,988 A | | 10/1977 | Doddi et al. |
| 4,175,555 A | | 11/1979 | Herbert |
| 4,262,665 A | * | 4/1981 | Roalstad .............. 606/72 |
| 4,275,717 A | | 6/1981 | Bolesky |
| 4,463,753 A | | 8/1984 | Gustilo |
| 4,632,101 A | * | 12/1986 | Freedland ............ 606/72 |
| 4,640,271 A | | 2/1987 | Lower |
| 4,667,663 A | | 5/1987 | Miyata |
| 4,688,561 A | | 8/1987 | Reese |
| 4,743,257 A | | 5/1988 | Tömälä |
| 4,790,304 A | | 12/1988 | Rosenberg |
| 4,796,612 A | | 1/1989 | Reese |
| 4,827,917 A | | 5/1989 | Brumfield |
| 4,873,976 A | | 10/1989 | Schreiber |
| 4,898,186 A | | 2/1990 | Ikada et al. |
| 4,903,692 A | | 2/1990 | Reese |
| 4,917,554 A | | 4/1990 | Bronn |
| 4,968,317 A | | 11/1990 | Törmälä |
| 4,978,349 A | | 12/1990 | Frigg |

(List continued on next page.)

FOREIGN PATENT DOCUMENTS

| | | |
|---|---|---|
| CH | 1156667 | 9/1998 |
| EP | 0 525352 A1 | 2/1993 |
| EP | 1 046 376 A1 | 4/2000 |

(List continued on next page.)

OTHER PUBLICATIONS

*Orthosorb® Absorbable Pin: Setting the Standard for Absorbable Internal Fixation for Shear or Torque Forces in the Foot, Hand, and Knee*, Product Information.

(List continued on next page.)

*Primary Examiner*—Todd E. Manahan
(74) *Attorney, Agent, or Firm*—Knobbe, Martens, Olson & Bear, LLP.

(57) ABSTRACT

Disclosed is a bone fixation device of the type useful for connecting soft tissue or tendon to bone or for connecting two or more bones or bone fragments together. The device comprises an elongate body having a distal anchor thereon. A proximal anchor is axially movably disposed with respect to the distal anchor, to accommodate different bone dimensions and permit appropriate tensioning of the fixation device. In one embodiment, the fixation device is optimized for construction from a biocompatible metal such as titanium, and the proximal anchor is removable to permit removal of the fixation device.

60 Claims, 7 Drawing Sheets

U.S. PATENT DOCUMENTS

| | | |
|---|---|---|
| 5,059,193 A | 10/1991 | Kuslich |
| 5,062,849 A | 11/1991 | Schelhas |
| 5,092,891 A | 3/1992 | Kummer et al. |
| 5,098,433 A | 3/1992 | Freedland |
| 5,122,141 A | 6/1992 | Simpson et al. |
| 5,167,663 A | 12/1992 | Brumfield |
| 5,167,664 A | 12/1992 | Hodorek |
| 5,217,462 A | 6/1993 | Asnis et al. |
| 5,242,447 A | 9/1993 | Borzone |
| 5,246,441 A | 9/1993 | Ross et al. |
| 5,250,049 A | 10/1993 | Michael |
| 5,300,074 A | 4/1994 | Frigg |
| 5,364,398 A | 11/1994 | Chapman et al. |
| 5,370,646 A | 12/1994 | Reese et al. |
| 5,449,359 A | 9/1995 | Groiso |
| 5,498,265 A | 3/1996 | Asnis et al. |
| 5,501,695 A | 3/1996 | Anspach, Jr. et al. |
| 5,536,127 A | 7/1996 | Pennig |
| 5,549,610 A | 8/1996 | Russell et al. |
| 5,618,142 A * | 4/1997 | Sonden et al. ............. 411/43 |
| 5,618,314 A * | 4/1997 | Harwin et al. ............. 606/72 |
| 5,626,613 A | 5/1997 | Schmieding |
| 5,628,751 A | 5/1997 | Sander et al. |
| 5,662,683 A | 9/1997 | Kay |
| 5,713,903 A * | 2/1998 | Sander et al. ............. 606/72 |
| 5,720,753 A | 2/1998 | Sander et al. |
| 5,725,541 A | 3/1998 | Anspach, III et al. |
| 5,728,097 A | 3/1998 | Mathews |
| 5,728,116 A | 3/1998 | Rosenman |
| 5,741,282 A | 4/1998 | Anspach, III et al. |
| 5,772,662 A | 6/1998 | Chapman et al. |
| 5,782,865 A * | 7/1998 | Grotz ..................... 606/72 |
| 5,849,004 A | 12/1998 | Bramlet |
| 5,871,485 A | 2/1999 | Rao et al. |
| 5,893,850 A | 4/1999 | Cachia |
| 5,904,696 A | 5/1999 | Rosenman |
| 5,908,422 A | 6/1999 | Bresina |
| 5,928,235 A | 7/1999 | Friedl |
| 5,928,244 A | 7/1999 | Tovey et al. |
| 5,935,129 A | 8/1999 | McDevitt et al. |
| 5,947,999 A | 9/1999 | Groiso |
| 5,948,000 A | 9/1999 | Larsen et al. |
| 5,954,747 A | 9/1999 | Clark |
| 5,957,924 A | 9/1999 | Törmäläet al. |
| 5,968,044 A | 10/1999 | Nicholson et al. |
| 5,976,139 A | 11/1999 | Bramlet |
| 5,984,927 A | 11/1999 | Wenstrom, Jr. et al. |
| 5,984,966 A | 11/1999 | Kiema et al. |
| 5,989,255 A | 11/1999 | Pepper et al. |
| 5,993,459 A | 11/1999 | Larsen et al. |
| 5,997,538 A | 12/1999 | Asnis et al. |
| 5,997,541 A | 12/1999 | Schenk |
| 6,001,100 A | 12/1999 | Sherman et al. |
| 6,001,101 A | 12/1999 | Augagneur et al. |
| 6,004,327 A | 12/1999 | Asnis et al. |
| 6,005,161 A | 12/1999 | Brekke et al. |
| 6,007,566 A | 12/1999 | Wenstrom, Jr. |
| 6,007,580 A | 12/1999 | Lehto et al. |
| 6,010,513 A | 1/2000 | Tormala et al. |
| 6,015,410 A | 1/2000 | Törmäläet al. |
| 6,019,762 A | 2/2000 | Cole |
| 6,036,701 A | 3/2000 | Rosenman |
| 6,068,648 A | 5/2000 | Cole et al. |
| 6,083,244 A | 7/2000 | Lubbers et al. |
| 6,126,661 A | 10/2000 | Faccioli et al. |
| 6,168,595 B1 | 1/2001 | Durham et al. |
| 6,183,474 B1 | 2/2001 | Bramlet et al. |
| 6,319,254 B1 | 11/2001 | Giet et al. |
| 6,482,210 B1 | 11/2002 | Skiba et al. |

FOREIGN PATENT DOCUMENTS

| | | |
|---|---|---|
| FR | 2 699 065 | 12/1992 |
| FR | 2 728 778 | 12/1994 |
| FR | 2 745 709 | 3/1996 |
| FR | 2 800 601 | 11/1999 |
| FR | 2 801 189 | 11/1999 |
| FR | 2 808 82 | 4/2000 |
| GB | 2157788 A | 10/1985 |
| GB | 2173565 A | 10/1986 |
| JP | 64-52439 | 2/1989 |
| RU | 1424823 A1 | 9/1988 |
| WO | WO 91/09572 | 12/1989 |

OTHER PUBLICATIONS

*Strength Starts With Simplicity, S D. sorb, Suture Anchor System . . . for Soft Tissue Retachment*, Surgical Dynamics™ Brochure 4–1997.

*So E–Z . . . So Secure, S D sorb E–Z Tac Implant, A fixation revolution for Soft Tissue Reattachment*, Surgical Dynamics™ Brochure 5–97.

*Eliminate Sutute Passing and Knot Tying with the E–Z Tac™ Soft Reattachment System*, http://www.surgicaldynamics.com/13354_body02.html.

*S D sorb ™, E–Z TAC™ Surgical Technique*, http://www.surgicaldynamics.com/13354_body03.html.

http://www.surgicaldynamics.con/images/ez-tac_bkg.JPG.

* cited by examiner

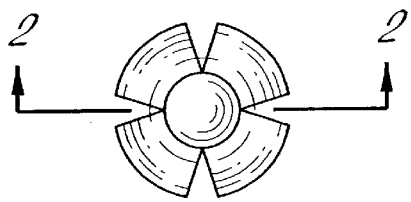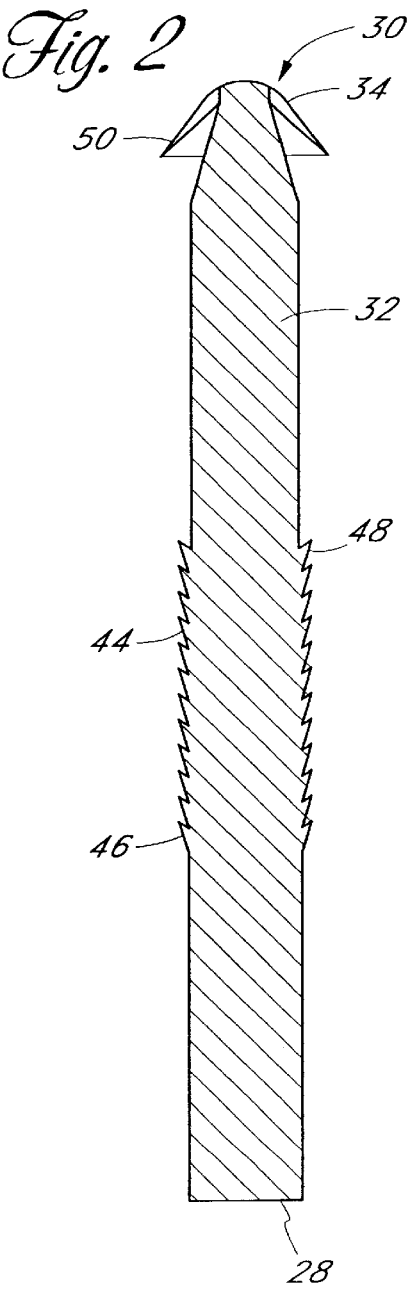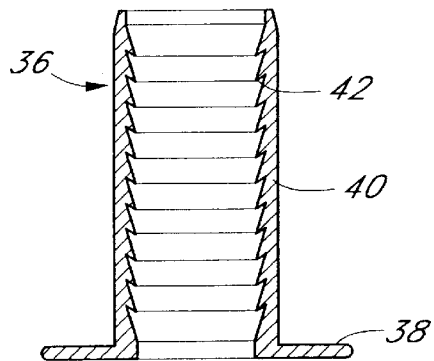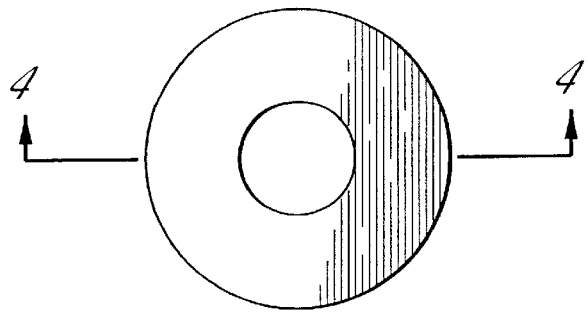

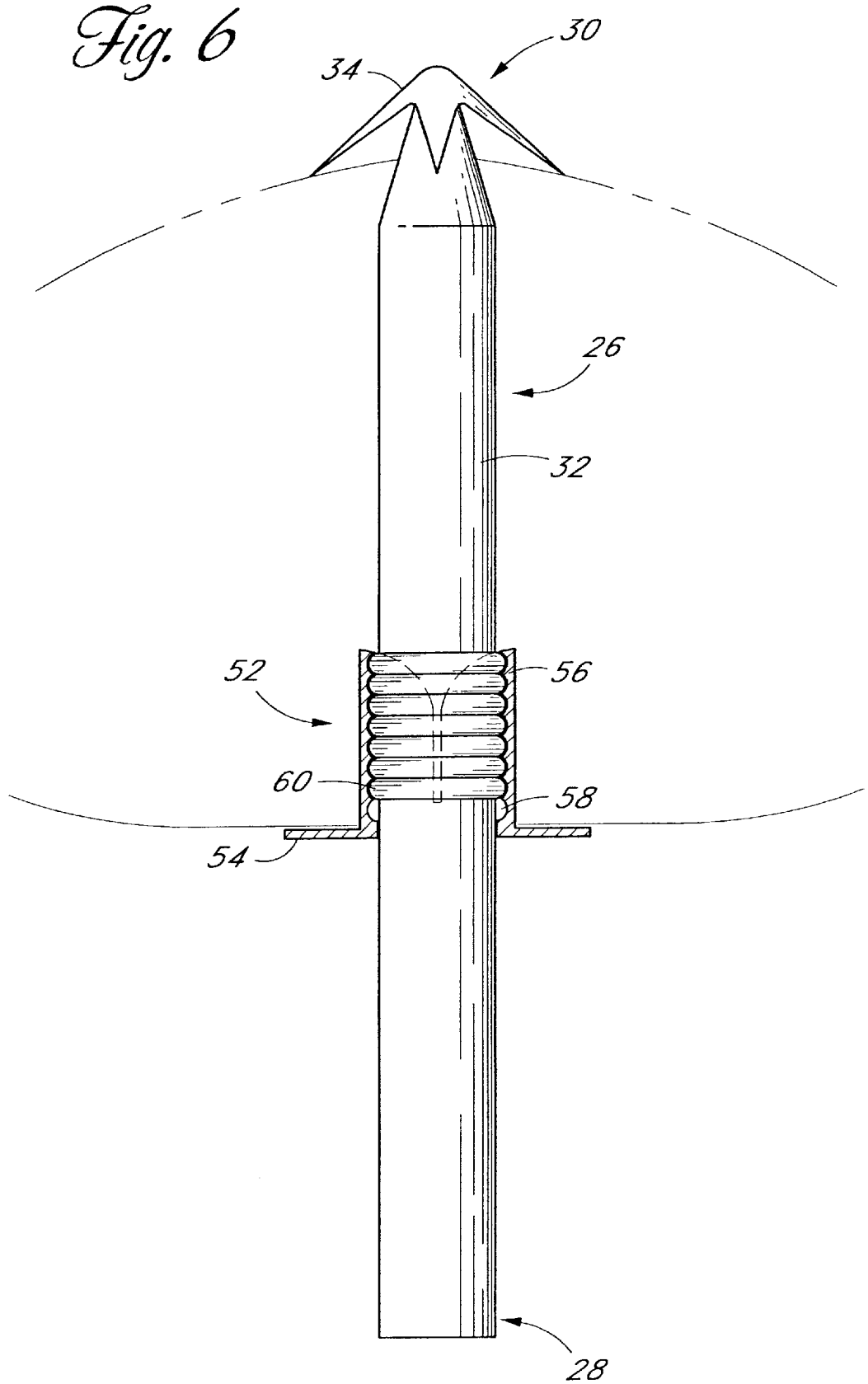

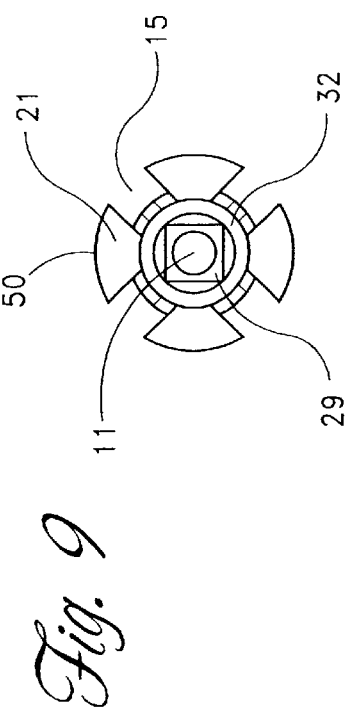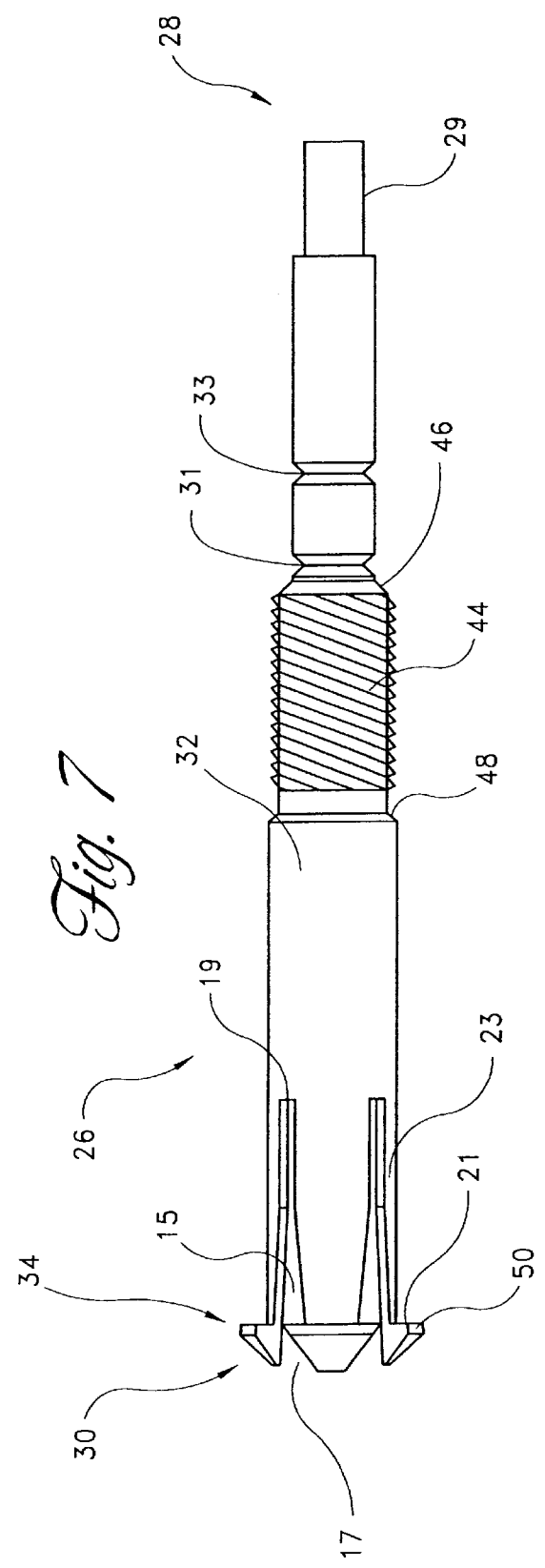

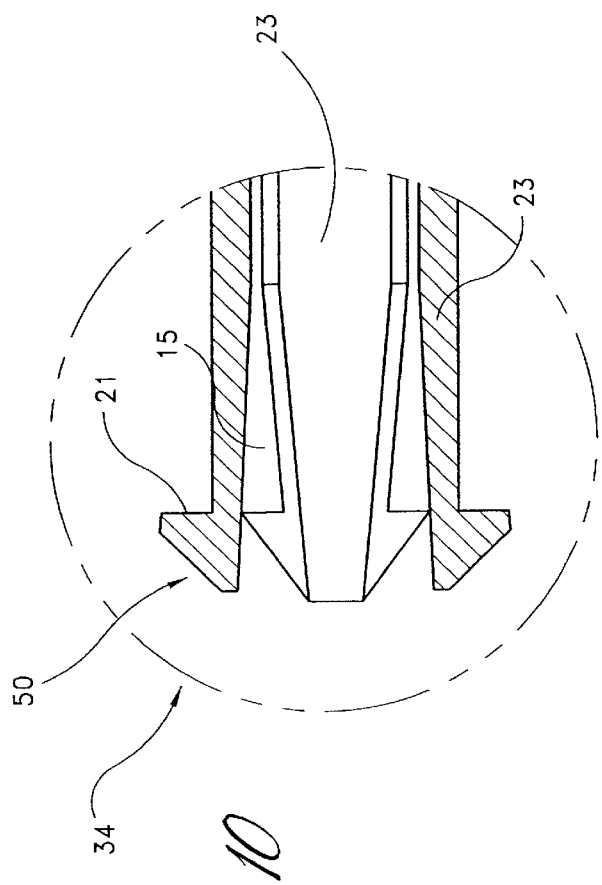
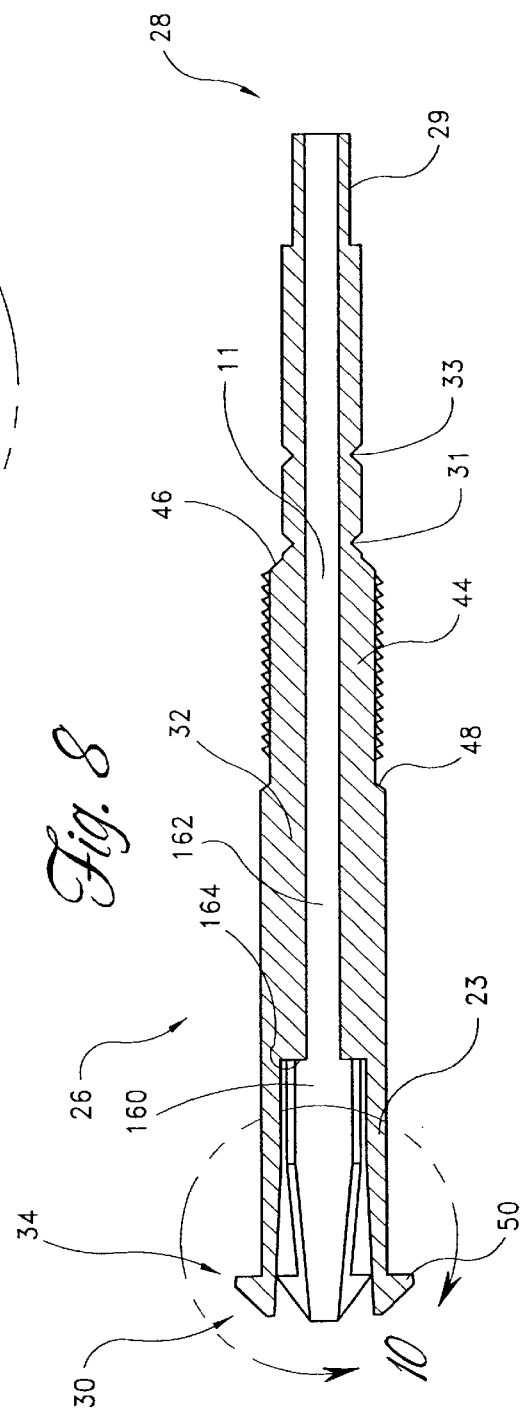

BONE FIXATION SYSTEM

This is a continuation-in-part of Ser. No. 09/558,057, filed on Apr. 26, 2000, abandoned which is a continuation-in-part of Ser. No. 09/266,138 filed on Mar. 10, 1999 abandoned which is a divisional of Ser. No. 08/745,652 filed on Nov. 12, 1996, now U.S. Pat. No. 5,893,850.

BACKGROUND OF THE INVENTION

The present invention relates to bone fixation systems and, more particularly, deployment devices and absorbable or nonabsorbable bone fixation pins of the type for fixing soft tissue or tendons to bone or for securing two or more adjacent bone fragments or bones together.

Bones which have been fractured, either by accident or severed by surgical procedure, must be kept together for lengthy periods of time in order to permit the recalcification and bonding of the severed parts. Accordingly, adjoining parts of a severed or fractured bone are typically clamped together or attached to one another by means of a pin or a screw driven through the rejoined parts. Movement of the pertinent part of the body may then be kept at a minimum, such as by application of a cast, brace, splint, or other conventional technique, in order to promote healing and avoid mechanical stresses that may cause the bone parts to separate during bodily activity.

The surgical procedure of attaching two or more parts of a bone with a pin-like device requires an incision into the tissue surrounding the bone and the drilling of a hole through the bone parts to be joined. Due to the significant variation in bone size, configuration, and load requirements, a wide variety of bone fixation devices have been developed in the prior art. In general, the current standard of care relies upon a variety of metal wires, screws, and clamps to stabilize the bone fragments during the healing process. Following a sufficient bone healing period of time, the percutaneous access site or other site may require re-opening to permit removal of the bone fixation device.

Long bone fractures are among the most common encountered in the human skeleton. Many of these fractures and those of small bones and small bone fragments must be treated by internal and external fixation methods in order to achieve good anatomical position, early mobilization, and early and complete rehabilitation of the injured patient.

The internal fixation techniques commonly followed today frequently rely upon the use of Kirschner wires (K-wires), intramedullary pins, wiring, plates, screws, and combinations of the foregoing. The particular device or combination of devices is selected to achieve the best anatomic and functional condition of the traumatized bone with the simplest operative procedure and with a minimal use of foreign-implanted stabilizing material. A variety of alternate bone fixation devices are also known in the art, such as, for example, those disclosed in U.S. Pat. No. 4,688,561 to Reese, U.S. Pat. No. 4,790,304 to Rosenberg, and U.S. Pat. No. 5,370,646 to Reese, et al.

Notwithstanding the common use of the K-wire to achieve shear-force stabilization of bone fractures, K-wire fixation is attended by certain known risks. For example, a second surgical procedure is required to remove the device after healing is complete. Removal is recommended, because otherwise the bone adjacent to an implant becomes vulnerable to stress shielding as a result of the differences in the modulus of elasticity and density between metal and the bone.

In addition, an implanted K-wire may provide a site for a variety of complications ranging from pin-tract infections to abscesses, resistant osteomyelitis, septic arthritis, and infected nonunion.

Another potential complication involving the use of K-wires is in vivo migration. Axial migration of K-wires has been reported to range from 0 mm to 20 mm, which can both increase the difficulty of pin removal as well as inflict trauma to adjacent tissue.

As conventionally utilized for bone injuries of the hand and foot, K-wires project through the skin. In addition to the undesirable appearance, percutaneously extending K-wires can be disrupted or cause damage to adjacent structures such as tendons if the K-wire comes into contact with external objects.

Notwithstanding the variety of bone fasteners that have been developed in the prior art, there remains a need for a bone fastener of the type that can accomplish shear-force stabilization with minimal trauma to the surrounding tissue both during installation and following bone healing.

In addition, there remains a need for a simple, adjustable bone fixation device which may be utilized to secure soft tissue or tendon to bone.

SUMMARY OF THE INVENTION

There is provided in accordance with one aspect of the present invention, a fixation pin for fixing bone to bone or other tissue to bone. The fixation pin comprises a body, having a proximal end and a distal end. A distal anchor is on the body. The distal anchor comprises at least a first retention surface on a first axially extending lever arm and a second retention surface on a second axially extending lever arm. Preferably, the first and second retention surfaces are laterally moveable between a first, implantation crossing profile and a second, larger, deployed crossing profile. The first and second retention structures are preferably biased in the direction of the second crossing profile. In certain embodiments, at least three retention surfaces and at least three lever arms are provided. The fixation pin may be integrally formed from a single piece of metal which may comprise titanium.

The fixation pin may further comprise a retention structure on the body, for retaining a proximal anchor. The retention structure may comprise a deviation in the surface of the body, such as an annular ridge, helical thread, or other recess or projection. A proximal anchor is movably carried by the body.

The fixation pin may additionally comprise at least one breakpoint on the body, for allowing a proximal projection of the body to be snapped off, following tensioning of the proximal anchor.

In accordance with another aspect of the present invention, there is provided a fixation pin for bone to bone or other tissue to bone fixation. The fixation pin comprises a tubular body, having a proximal end and a distal end. At least two slots are provided in the tubular body, extending proximally from the distal end to define at least a first and a second axially extending lever arms. A proximally facing retention surface is carried by each lever arm. A retention structure is also provided on the body, for removably carrying a proximal anchor. The first and second retention surfaces are laterally moveable between an implantation crossing profile and a deployed crossing profile.

The retention structure may comprise a thread on the body, proximal to at least a portion of the lever arms. A proximal anchor is movably carried by the thread.

In accordance with another aspect of the present invention, there is provided a method of fixing a first material to bone. The method comprises the steps of providing a pin having a distal anchor and at least one proximal breakpoint. The distal anchor is advanced through the first material and into the bone. A proximal anchor is advanced distally along the pin to secure the first material to the bone. Lateral pressure is applied to a proximal portion of the pin, to break the pin at the breakpoint.

In one application of the method, the first material comprises bone. In alternate applications, the first material comprises soft tissue, tendon, graft or other synthetic or natural biological material.

In one application, the advancing the distal anchor step comprises advancing the distal anchor all the way through the bone. The advancing a proximal anchor step may comprise rotating the proximal anchor with respect to the pin.

The method may further comprise the step of removing the proximal anchor by rotating the proximal anchor with respect to the pin. A core drill may thereafter be advanced over the pin, and the pin removed from the bone.

In accordance with another aspect of the present invention, there is provided a fixation pin for fixing a first material to bone. The pin comprises an elongate tubular body, having a proximal end and a distal end. A plurality of deflectable barbs are carried by the distal end. A thread is provided on the tubular body, in-between the proximal end and the distal end, and a break point is provided on the tubular body, proximal to at least a portion of the thread.

The pin may further comprise a proximal anchor, removably retained on the tubular body by the thread. A rotational coupling is provided on the pin, for coupling to a tool. A second rotational coupling is provided on the anchor, to permit rotation of the anchor while resisting rotation of the pin. Each of the barbs may be attached to the tubular body by an axially extending lever arm.

Further features and advantages of the present invention will become apparent to those of skill in the art in view of the detailed description of preferred embodiments which follows, when considered together with the attached claims and drawings.

BRIEF DESCRIPTION OF THE DRAWINGS

FIG. 2 is a longitudinal cross-sectional view through the pin body of the present invention.

FIG. 3 is a distal end elevational view of the pin body of FIG. 2.

FIG. 4 is a longitudinal cross-sectional view of the proximal anchor of the bone fixation device.

FIG. 5 is a proximal end elevational view of the proximal anchor of the bone fixation device.

FIG. 6 is a side elevational view of an alternate embodiment of the bone fixation device of the present invention.

FIG. 7 is a side elevational view of an alternate embodiment of the pin body in accordance with the present invention.

FIG. 8 is a longitudinal cross-sectional view through the pin body of FIG. 7.

FIG. 9 is a distal end elevational view of the pin body of FIG. 7.

FIG. 10 is an enlarged detail view of the distal end of the device shown in FIG. 8.

DETAILED DESCRIPTION OF PREFERRED EMBODIMENTS

Figure 1:
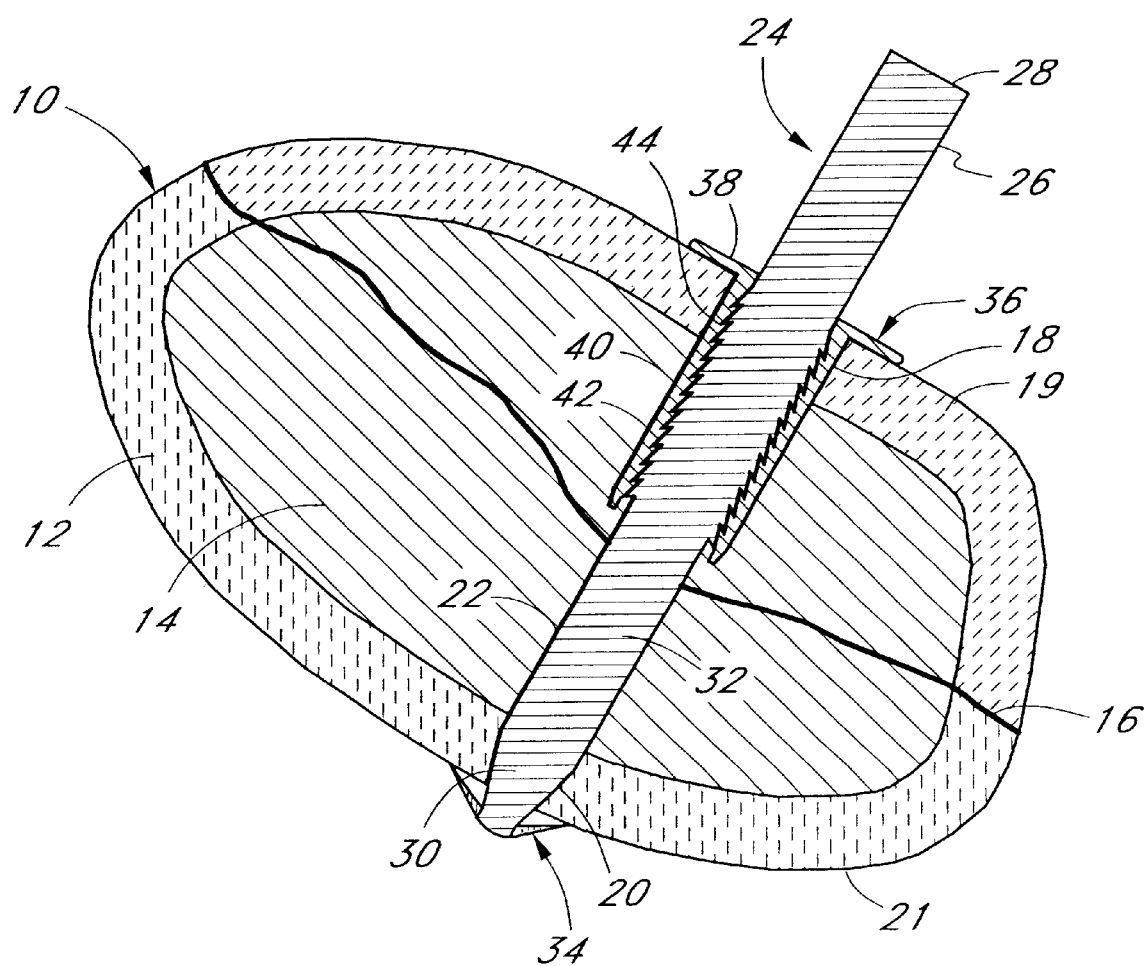
FIG. 1 is a cross-sectional schematic view of a bone fixation device of the present invention positioned within a fractured bone.

Although the application of the present invention will be disclosed in connection with the simplified bone fracture of FIG. 1, the methods and structures disclosed herein are intended for application in any of a wide variety of bones and fractures, as will be apparent to those of skill in the art in view of the disclosure herein. For example, the bone fixation device of the present invention is applicable in a wide variety of fractures and osteotomies in the hand, such as interphalangeal and metacarpophalangeal arthrodesis, transverse phalangeal and metacarpal fracture fixation, spiral phalangeal and metacarpal fracture fixation, oblique phalangeal and metacarpal fracture fixation, intercondylar phalangeal and metacarpal fracture fixation, phalangeal and metacarpal osteotomy fixation as well as others known in the art. A wide variety of phalangeal and metatarsal osteotomies and fractures of the foot may also be stabilized using the bone fixation device of the present invention. These include, among others, distal metaphyseal osteotomies such as those described by Austin and Reverdin-Laird, base wedge osteotomies, oblique diaphyseal, digital arthrodesis as well as a wide variety of others that will be known to those of skill in the art. The bone fixation device may be used with or without plate(s) or washer(s), all of which can be either permanent or absorbable.

Fractures of the fibular and tibial malleoli, pilon fractures and other fractures of the bones of the leg may be fixated and stabilized with the present invention with or without the use of plates, both absorbable or non-absorbing types, and with alternate embodiments of the current invention. One example is the fixation of the medial malleolar avulsion fragment fixation with the radially and axially expanding compression device. Each of the foregoing may be treated in accordance with the present invention, by advancing one of the fixation devices disclosed herein through a first bone component, across the fracture, and into the second bone component to fix the fracture.

The fixation device of the present invention may also be used to attach tissue or structure to the bone, such as in ligament reattachment and other soft tissue attachment procedures. Plates and other implants may also be attached to bone, using either resorbable or nonresorbable fixation devices disclosed herein depending upon the implant and procedure. The fixation device may also be used to attach sutures to the bone, such as in any of a variety of tissue suspension procedures.

For example, peripheral applications for the fixation devices include utilization of the device for fastening soft tissue such as capsule, tendon or ligament to bone. It may also be used to attach a synthetic material such as marlex mesh, to bone or allograft material such as tensor fascia lata, to bone. In the process of doing so, retention of the material to bone may be accomplished with the collar as shown, with an enlarged collar to increase contact surface area, or the pin and or collar may be modified to accept a suture or other material for facilitation of this attachment.

Specific examples include attachment of the posterior tibial tendon to the navicular bone in the Kidner operation.

Navicular-cuneiform arthrodesis may be performed utilizing the device and concurrent attachment of the tendon may be accomplished. Attachment of the tendon may be accomplished in the absence of arthrodesis by altering the placement of the implant in the adjacent bone.

Ligament or capsule reattachment after rupture, avulsion of detachment, such as in the ankle, shoulder or knee can also be accomplished using the devices disclosed herein.

The fixation devices may be used in combination with semi tubular, one-third tubular and dynamic compression plates, both of metallic and absorbable composition, preferably by modifying the collar to match the opening on the plate.

The canulated design disclosed below can be fashioned to accept an antibiotic impregnated rod for the slow release of medication and/or bone growth or healing agents locally. This may be beneficial for prophylaxis, especially in open wounds, or when osteomyelitis is present and stabilization of fracture fragments is indicated.

A kit may be assembled for field use by military or sport medical or paramedical personnel. This kit contains an implanting tool, and a variety of implant device size and types, a skin stapler, bandages, gloves, and basic tools for emergent wound and fracture treatment. Antibiotic rods would be included for wound prophylaxis during transport.

Referring to FIG. 1, there is illustrated generally a bone 10, shown in cross-section to reveal an outer cortical bone component 12 and an inner cancellus bone component 14. A fracture 16 is schematically illustrated as running through the bone 10 to at least partially divide the bone into what will for present purposes be considered a proximal component 19 and distal component 21. The fracture 16 is simplified for the purpose of illustrating the application of the present invention. However, as will be understood by those of skill in the art, the fracture 16 may extend through the bone at any of a wide variety of angles and depths. The bone fixation device of the present invention may be useful to stabilize two or more adjacent components of bone as long as each component may be at least partially traversed by the bone fixation device and anchored at opposing sides of the fracture to provide a sufficient degree of stabilization.

A proximal aperture 18 is provided in the proximal component 19 of the bone 10, such as by drilling, as will be discussed. A distal aperture 20 is provided in an opposing portion of bone such as in distal bone component 21 and is connected to the proximal aperture 18 by way of a through hole 22, as is known in the art, in a through hole application. The fixation device may also be useful in certain applications where the distal end of the device resides within the bone.

The bone fixation device 24 is illustrated in FIG. 1 in its installed position within the through hole 22. The bone fixation device 24 generally comprises an elongate pin 26 having a proximal end 28, a distal end 30, and an elongate pin body 32 extending therebetween.

The distal end 30 of pin 26 is provided with a distal anchor 34, as will be discussed. A proximal anchor 36 is also provided, such as a radially outwardly extending collar 38 connected to a tubular housing 40 adapted to coaxially receive the pin body 32 therethrough.

The radially interior surface of the tubular housing 40, in the illustrated embodiment, is provided with a plurality of retention structures 42. Retention structures 42 cooperate with corresponding retention structures 44 on the surface of pin body 32 to permit advancement of the proximal anchor 36 in the direction of the distal anchor 34 for properly sizing and tensioning the bone fixation device 24. Retention structures 42 then cooperate with retention structures 44 to provide a resistance to movement of the proximal anchor 36 in the proximal direction relative to pin body 32.

In use, the proximal projection of pin 26 which extends beyond the proximal anchor 36 after tensioning is preferably removed, such as by cutting, to minimize the projection of the bone fixation device 24 from the surface of the bone.

One embodiment of the pin 26, adapted for fixing oblique fractures of the fibula or metatarsal bone(s) is illustrated in FIG. 2. The bone fixation device 24 of this embodiment uses a generally cylindrical pin body 32. Although the present invention is disclosed as embodied in a pin body 32 having a generally circular cross section, cross sections such as oval, rectangular, square or tapered to cause radial along with axial bone compression or other configurations may also be used as desired for a particular application.

Pin body 32 generally has an axial length of within the range of from about 5 mm or about 10 mm to about 70 mm in the as-manufactured condition. In one embodiment intended for small bones in the foot, the pin body 32 has an axial length of about 19 mm. The illustrated embodiment shows a solid pin body 32. However, a cannulation may be provided along the longitudinal axis of the body to allow introduction of the pin over a wire as is understood in the art. Hollow tubular structures may also be used.

The retention structures 44 on the surface of pin body 32 in the illustrated embodiment comprise a plurality of annular ramp or ratchet-type structures which permit the proximal anchor 36 to be advanced in a distal direction with respect to pin body 32, but which resist proximal motion of proximal anchor 36 with respect to pin body 32. Any of a variety of ratchet-type structures can be utilized in the present invention. The annular ramped rings illustrated in FIG. 2 provide, among other advantages, the ability of the ratchet to function regardless of the rotational orientation of the proximal anchor 36 with respect to the pin body 32. In an embodiment having a noncircular cross section, or having a rotational link such as an axially-extending spline on the pin body 32 for cooperating with a complementary keyway on proximal anchor 36, the retention structures 42 can be provided on less than the entire circumference of the pin body as will be appreciated by those of skill in the art. Thus, ratchet structures can be aligned in an axial strip such as at the bottom of an axially extending channel in the surface of the pin body.

A single embodiment of the bone fixation device can be used for fixing fractures in bones having any of a variety of diameters. This is accomplished by providing the retention structures 44 over a predetermined axial working length of the pin body 32. For example, in the illustrated embodiment, the retention structures 44 commence at a proximal limit 46 and extend axially until a distal limit 48. Axially extending the retention zone between limits 46 and 48 will extend the effective range of bone thicknesses which the pin 32 can accommodate. Although the retention structures 44 may alternatively be provided throughout the entire length of the pin body 32, retention structures 44 may not be necessary in the most distal portions of pin body 32 in view of the minimum diameter of bones likely to be fixed.

In one embodiment of the invention, the distal limit 48 of retention structures 44 is spaced apart from the distal end 30 of pin body 32 by a distance within the range of from about 4 mm to about 20 mm, and, in embodiments for small bones in the foot, from about 4 mm to about 8 mm. The axial length of the portion of the pin body 32 having retention structures 44 thereon, from proximal limit 46 to distal limit 48, is generally within the range of from about 4 mm to about 8 mm, and was approximately 6 mm in an embodiment having a pin body length of about 19 mm. Depending upon the anchor design, the zone between proximal limit 46 and distal limit 48 may extend at least about 50%, and in some embodiments in excess of about 75% or even in excess of 90% of the length of the pin body.

In general, the minimum diameter of the pin body 32 is a function of the construction material of the pin and the desired tensile strength for a given application. The maximum diameter is established generally by the desire to minimize the diameter of the through hole 22 while still preserving a sufficient structural integrity of the fixation device 24 for the intended application.

The diameter of pin body 32 will generally be in the range of from about 1.5 mm or 1.8 mm for small bones of the foot and hand to as large as 7.0 mm or larger for bones such as the tibia. In one absorbable embodiment of the invention intended for use in the first metatarsal, the pin 24 comprises poly-p-dioxanone and has a diameter of about 1.8 mm. Any of a variety of other materials may also be used, as discussed infra.

The distal anchor 34 in the illustrated embodiment comprises a plurality of ramped extensions 50 which incline radially outwardly in the proximal direction. Extensions 50 are positioned or compressible radially inwardly for the purpose of advancing the pin 32 into, and, in some applications, through the through hole 22. Extensions 50 preferably exert a radially outwardly directed bias so that they tend to extend radially outwardly from the pin body 32 once the distal anchor 34 has advanced out through the distal aperture 20 in bone 10. Proximal traction on the proximal end 28 of pin body 32 will thereafter tend to cause extensions 50 to seat firmly against the outside surface of distal bone component 21, as illustrated in FIG. 1. In accordance with an optional feature which can be included in any of the embodiments herein, the pin body 32 is provided with a central lumen extending axially therethrough (cannulated) for introduction over a guide pin as will be understood by those of skill in the art.

Although any of a variety of alternate designs for distal anchor 34 may be utilized in the context of the present invention, any such distal anchors 34 preferably permit axial distal motion of pin body 32 through the through hole 22, and thereafter resist proximal withdrawal of the pin body 32 from through hole 22. As will be appreciated by those of skill in the art, this feature allows the bone fixation device 24 to be set within a bone through a single proximal percutaneous puncture or incision, without the need to expose the distal component 21 or "backside" of the bone. This can be accomplished by biased anchors which are formed integrally with the pin, or which are attached during manufacturing. Distal anchors may also be hinged to the pin body, and may be deployed by a push or pull wire extending through the pin body if the desired construction material does not permit adequate spring bias.

For a through hole having a diameter of about 2.3 mm, pin bodies 32 having an outside diameter of about 1.8 mm in the areas other than retention structures 44, and a maximum outside diameter of about 2.24 mm in the area of retention structures 44 have been found to be useful. In this embodiment, the maximum outside diameter of the distal anchor 34 was approximately 2.92 mm in the relaxed state. The axial length from the distal tip of distal end 30 to the proximal extent of extensions 50 was about 1.21 mm.

The pin body 32, together with the distal anchor 34 and other components of the present invention can be manufactured in accordance with any of a variety of techniques which are well known in the art, using any of a variety of medical-grade construction materials. For example, the pin body 32 and other components of the present invention can be injection-molded from a variety of medical-grade polymers including high or other density polyethylene, nylon and polypropylene. Distal anchor 34 can be separately formed from the pin body 32 and secured thereto in a post-molding operation, using any of a variety of securing techniques such as solvent bonding, thermal bonding, adhesives, interference fits, pivotable pin and aperture relationships, and others known in the art. Preferably, however, the distal anchor 34 is integrally molded with the pin body 32, if the desired material has appropriate physical properties.

Retention structures 44 can also be integrally molded with the pin body 32. Alternatively, retention structures 44 can be machined or pressed into the pin body 32 in a post-molding operation, or secured using other techniques depending upon the particular design.

A variety of polymers which may be useful for the anchor components of the present invention are identified below. Many of these polymers have been reported to be biodegradable into water-soluble, non-toxic materials which can be eliminated by the body:

Polycaprolactone
Poly(L-lactide)
Poly(DL-lactide)
Polyglycolide
Poly(L-Lactide-co-D, L-Lactide)
70:30 Poly(1-Lactide-co-D, L-Lactide)
95:5 Poly(DL-lactide-co-glycolide)
90:10 Poly(DL-lactide-co-glycolide)
85:15 Poly(DL-lactide-co-glycolide)
75:25 Poly(DL-lactide-co-glycolide)
50:50 Poly(DL-lactide-co-glycolide)
90:10 Poly(DL-lactide-co-caprolactone)
75:25 Poly(DL-lactide-co-caprolactone)
50:50 Poly(DL-lactide-co-caprolactone)
Polydioxanone
Polyesteramides
Copolyoxalates
Polycarbonates
Poly(glutamic-co-leucine)

The desirability of any one or a blend of these or other polymers can be determined through routine experimentation by one of skill in the art, taking into account the mechanical requirements, preferred manufacturing techniques, and desired reabsorption time. Optimization can be accomplished through routine experimentation in view of the disclosure herein.

Alternatively, the anchor components can be molded, formed or machined from biocompatible metals such as Nitinol, stainless steel, titanium, and others known in the art. In one embodiment, the components of the bone fixation device 24 are injection-molded from a bioabsorbable material, to eliminate the need for a post-healing removal step. One suitable bioabsorbable material which appears to exhibit sufficient structural integrity for the purpose of the present invention is poly-p-dioxanone, such as that available from the Ethicon Division of Johnson & Johnson. Poly-L-lactide, or blends of the two may alternatively be used. As used herein, terms such as bioabsorbable, bioresorbable and biodegradable interchangeably refer to materials which will dissipate in situ, following a sufficient bone healing period of time, leaving acceptable byproducts.

The bioabsorbable implants of this invention can be manufactured in accordance with any of a variety of techniques known in the art, depending upon the particular polymers used, as well as acceptable manufacturing cost and dimensional tolerances as will be appreciated by those of skill in the art in view of the disclosure herein. For example, any of a variety of bioabsorbable polymers, copolymers or polymer mixtures can be molded in a single compression molding cycle, or the surface structures can be machined on the surface of the pin or sleeve after the molding cycle. It is also possible to use the techniques of U.S. Pat. No. 4,743,257, the entire disclosure of which is incorporated herein by reference, to mold absorbable fibers and binding polymers together, to create a fiber-reinforced absorbable anchor.

An oriented or self-reinforced structure for the anchor can also be created during extrusion or injection molding of absorbable polymeric melts through a suitable die or into a suitable mold at high speed and pressure. When cooling occurs, the flow orientation of the melt remains in the solid material as an oriented or self-reinforcing structure. The mold can have the form of the finished anchor component, but it is also possible to manufacture the anchor components of the invention by machining injection-molded or extruded semifinished products. It may be advantageous to make the anchors from melt-molded, solid state drawn or compressed, bioabsorbable polymeric materials, which are described, e.g., in U.S. Pat. Nos. 4,968,317 and 4,898,186, the entire disclosures of which are incorporated herein by way of this reference.

Reinforcing fibers suitable for use in the anchor components of the present invention include ceramic fibers, like bioabsorbable hydroxyapatite or bioactive glass fibers. Such bioabsorbable, ceramic fiber reinforced materials are described, e.g., in published European Patent Application No. 0146398 and in WO/96/21628, the entire disclosures of which are incorporated herein by way of this reference.

As a general feature of the orientation, fiber-reinforcement or self-reinforcement of the anchor components, many of the reinforcing elements are oriented in such a way that they can carry effectively the different external loads (such as tensile, bending and shear loads) that are directed to the anchor as used.

The oriented and/or reinforced anchor materials for many applications have tensile strengths in the range of about 100–2000 MPa, bending strengths in the range of about 100–600 MPa and shear strengths in the range of about 80–400 MPa, optimized for any particular design and application. Additionally, they are relatively stiff and tough. These mechanical properties may be superior to those of non-reinforced or non-oriented absorbable polymers, which often show strengths between about 40 and 100 MPa and are additionally may be flexible or brittle. See, e.g., S. Vainionpaa, P. Rokkanen and P. Tormnld, "Surgical Applications of Biodegradable Polymers in Human Tissues", Progr. Polym. Sci., Vol. 14, (1989) at 679–716, the full disclosure of which is incorporated herein by way of this reference.

The anchor components of the invention (or a bioabsorbable polymeric coating layer on part or all of the anchor surface), may contain one or more bioactive substances, such as antibiotics, chemotherapeutic substances, angiogenic growth factors, substances for accelerating the healing of the wound, growth hormones, antithrombogenic agents, bone growth accelerators or agents, and the like. Such bioactive implants may be desirable because they contribute to the healing of the injury in addition to providing mechanical support.

In addition, the anchor components may be provided with any of a variety of structural modifications to accomplish various objectives, such as osteoincorporation, or more rapid or uniform absorption into the body. For example, osteoincorporation may be enhanced by providing a micropitted or otherwise textured surface on the anchor components. Alternatively, capillary pathways may be provided throughout the pin and collar, such as by manufacturing the anchor components from an open cell foam material, which produces tortuous pathways through the device. This construction increases the surface area of the device which is exposed to body fluids, thereby generally increasing the absorption rate. Capillary pathways may alternatively be provided by laser drilling or other technique, which will be understood by those of skill in the art in view of the disclosure herein. In general, the extent to which the anchor can be permeated by capillary pathways or open cell foam passageways may be determined by balancing the desired structural integrity of the device with the desired reabsorption time, taking into account the particular strength and absorption characteristics of the desired polymer.

One open cell bioabsorbable material is described in U.S. Pat. No. 6,005,161 as a poly(hydroxy) acid in the form of an interconnecting, open-cell meshwork which duplicates the architecture of human cancellous bone from the iliac crest and possesses physical property (strength) values in excess of those demonstrated by human (mammalian) iliac crest cancellous bone. The gross structure is said to maintain physical property values at least equal to those of human, iliac crest, cancellous bone for a minimum of 90 days following implantation. The disclosure of U.S. Pat. No. 6,005,161 is incorporated by reference in its entirety herein.

The anchors of the present invention may be sterilized by any of the well known sterilization techniques, depending on the type of material. Suitable sterilization techniques include heat sterilization, radiation sterilization, such as cobalt 60 irradiation or electron beams, ethylene oxide sterilization, and the like.

In the embodiment illustrated in FIG. 4, the proximal anchor 36 comprises a collar 38 for contacting the proximal bone component 19. Collar 38 preferably comprises a radially-outwardly extending annular flange to optimize contact with the proximal bone component 19. Alternatively, proximal collar 38 may comprise one or more radially-outwardly extending stops, a frusto-conical plug, or other structures which stop the distal progress of proximal anchor 36 with respect to the through hole 22 or blind hole, depending upon the application.

The pin body 32 cooperates with a proximal anchor 36 to accomplish the fixation function of the present invention. Proximal anchor 36 is preferably axially movably carried by the pin body 32 throughout a sufficient axial range of motion to accommodate a variety of bone diameters.

Collar 38 is axially movably disposed with respect to pin body 32 such as by connection to a tubular housing 40. Tubular housing 40 is concentrically positioned on pin body 32, and is provided on its interior surface with at least one, and preferably a plurality, of retention structures 42. Retention structures 42 are configured to cooperate with the complementary retention structures 44 on the pin body 32 to permit axial distal advancement of collar 38 with respect to pin body 32, but resist proximal motion of collar 38 with respect to pin body 32, as has been discussed.

In one embodiment of the present invention, the minimum interior diameter of the tubular housing 40 is about 2.00 mm. The maximum interior diameter of the tubular housing 40, at the radial outwardmost bottom of the annular recesses adapted to cooperate with annular ridges 44 on pin body 32, is about 2.17 mm. The outside diameter of the collar 38 is about 2.70 mm, and the thickness in the axial direction of annular collar 38 is about 0.20 mm.

The retention structures 42 may comprise any of a variety of complementary surface structures for cooperating with the corresponding structures 44 on the pin 32, as is discussed elsewhere herein. In the illustrated embodiment, the retention structures are in the form of a plurality of annular rings or helical threads, which extend axially throughout the length of the tubular housing 40. The retention structure 42 may alternatively comprise a single thread, ridge or groove or a plurality of structures which extend only part way (e.g., at least about 10% or 25% or more) along the length of the tubular housing 40. Retention force may be optimized by providing threads or other structures along a substantial portion, e.g., throughout at least 75% or 80% of the axial length of the tubular housing 40.

The overall length of the tubular housing 40 may be maximized with respect to the depth of the target borehole for a particular application. For example, in a device intended to fix bones having a diameter within the range of from about 15–20 mm, the axial length of the tubular body 40 is preferably at least about 8 mm or 10 mm, and, more preferably, at least about 12 mm or 14 mm. In this manner, the axial length of the zone of retention structures 42 is maximized, thereby increasing the tensile strength of the implanted device. The proximal anchor 36 can be readily constructed using other dimensions and configurations while still accomplishing the desired function, as will be apparent to those of skill in the art in view of the disclosure herein.

In use, a bone is first identified having a fracture which is fixable by a pin-type fixation device. The clinician assesses the bone, selects a bone drill and drills a through hole 22 in accordance with conventional techniques.

A bone fixation device 24 having an axial length and outside diameter suitable for the through hole 22 is selected. The distal end 30 of the bone fixation device 24 is percutaneously or otherwise advanced towards the bone, and subsequently advanced through the through hole 22 until distal anchor 34 exits the distal aperture 20. The proximal anchor 36 may be positioned on the bone fixation device 24 prior to positioning of the pin body 32 in the through hole 22, or following placement of the pin body 32 within through hole 22.

Proximal traction is applied to the proximal end 28 of pin body 32, to seat the distal anchor 34. While proximal traction is applied to the proximal end 28 of pin body 32, such as by conventional hemostats or a calibrated loading device, the proximal anchor 36 is advanced distally until the anchor 36 fits snugly against the proximal component 19 of the bone. Appropriate tensioning of the bone fixation device 24 is accomplished by tactile feedback or through the use of a calibration device for applying a predetermined load on implantation.

Following appropriate tensioning of the proximal anchor 36, the proximal end 28 of the pin body 32 is preferably cut off and removed. Pin body 32 may be cut using conventional bone forceps which are routinely available in the clinical setting.

Following trimming the proximal end 28 of pin 26, the access site may be closed and dressed in accordance with conventional wound closure techniques.

Preferably, the clinician will have access to an array of bone fixation devices 24, having different diameters and axial lengths. These may be packaged one or more per package in sterile envelopes or peelable pouches, or in dispensing cartridges which may each hold a plurality of devices 24. Upon encountering a bone for which the use of a fixation device is deemed appropriate, the clinician will assess the dimensions and load requirements of the bone, and select a bone fixation device from the array which meets the desired specifications.

Referring to FIG. 6, there is disclosed an alternate embodiment of the fixation pin. The fixation pin 26 illustrated in FIG. 6 may be identical to the embodiments previously discussed, except with respect to the proximal anchor 52. Proximal anchor 52 comprises a radially outwardly extending annular collar 54 or other structure for resisting motion of the proximal anchor 52 in a distal direction through the aperture in the bone. Collar 54 is connected to a proximal portion of the tubular housing 56, analogous to housing 40 previously discussed. Tubular housing 56 is adapted to receive the pin body 32 therethrough.

The radially inwardly facing surface of tubular housing 56 is provided with a plurality of retention structures 58. In this embodiment, retention structures 58 comprise a plurality of recesses or grooves which extend radially outwardly into the tubular housing 56. Retention structures 58 are adapted to cooperate with corresponding retention structure 60 secured to or integral with the pin 32. Retention structure 60 in this embodiment comprise a plurality of radially outwardly extending annular rings or threads, which are adapted to be received within the corresponding retention structures 58. In this embodiment, the proximal anchor 52 is unable to move in an axial direction with respect to pin 32 unless sufficient axial force is applied to plastically-deform the retention structures 58 and/or retention structures 60 so that the tubular housing 56 snaps, ridge by ridge, in the direction of the axial force. The precise amount of axial force necessary to overcome the resistance to motion of proximal anchor 52 with respect to pin 32 can be optimized through appropriate tolerancing of the corresponding retention structures, together with the selection of materials for the proximal anchor 52 and/or pin 32. Preferably, the tolerances and construction details of the corresponding retention structures 58 and 60 are optimized so that the proximal anchor 52 may be advanced distally over the pin 32 using manual force or an installation tool, and the proximal anchor 52 will have a sufficient retention force to resist movement of the bone fragments under anticipated use conditions.

Referring to FIGS. 7–14, there is illustrated an alternate embodiment of the fixation device of the present invention. This embodiment is optimized for construction from a metal, such as titanium or titanium alloy, although other materials including those disclosed elsewhere herein may be utilized for the present embodiment. Referring to FIGS. 7 and 8, the fixation device includes a body 32 which is in the form of a pin 26 extending between a proximal end 28 and a distal end 30. The distal end 30 includes a plurality of friction enhancing or interference fit structures such as ramped extensions or barbs 50, for engaging the distal cortical bone or other surface or interior cancellous bone as has been described.

Although the illustrated embodiment includes four barbs 50, oriented at 90° with respect to each other, anywhere from one to about twelve or more barbs 50 may be utilized as will be apparent to those of skill in the art in view of the disclosure herein. The barbs 50 may be radially symmetrically distributed about the longitudinal axis of the pin 26. Each barb 50 is provided with a transverse engagement surface 21, for contacting the distal surface of the cortical bone or other structure or surface against which the barb 50 is to anchor. Transverse engagement surfaces 21 may lie on a plane which is transverse to the longitudinal axis of the pin 26, or may be inclined with respect to the longitudinal axis of the pin 26.

Each of the transverse engagement surfaces 21 in the illustrated embodiment lies on a common plane which is transverse to the longitudinal axis of the pin 26. Two or more planes containing engagement surfaces 21 may alternatively be provided. The transverse engagement surfaces 21 may also lie on one or more planes which are non-normal to the longitudinal axis of pin 26. For example, the plane of a plurality of transverse engagement surfaces 21 may be inclined at an angle within the range of from about 35° or 45° to about 90° with respect to the longitudinal axis of the pin 26. The plane of the transverse engagement surface may thus be selected to take into account the angle of the distal surface of the bone through which the pin may be positioned, as may be desired in certain clinical applications.

In order to facilitate the radially inward compression of the barbs 50 during the implantation process, followed by radially outward movement of the barbs 50 to engage the distal bone surface, each barb 50 in the illustrated embodiment is carried by a flexible or hinged lever arm 23. Lever arms 23 may be formed by creating a plurality of axial slots 15 in the sidewall of the pin 26. The axial slots 15 cooperate with a central lumen 11 to isolate each barb 50 on a unique lever arm 23. The axial length of the axial slots 15 may be varied, depending upon the desired length over which flexing is desirably distributed, the desired range of lateral motion, and may vary depending upon the desired construction material. For a relatively rigid material such as titanium, axial lengths of the axial slot 15 in excess of about 0.1 inches and preferably in excess of about 0.2 inches are utilized on a pin 26 having an outside diameter of about 0.1 inches and a length of about 1.25 inches. Axial slots 15 will generally extend within a range of from about 5% to about 90%, and often within about 10% to about 30% of the overall length of the pin 26.

The circumferential width of the slots 15 at the distal end 30 is selected to cooperate with the dimensions of the barbs 50 to permit radial inward deflection of each of the barbs 50 so that the pin 26 may be press fit through a predrilled hole having an inside diameter approximately equal to the outside diameter of the pin 26 just proximal to the transverse engagement surfaces 21. For this purpose, each of the slots 15 tapers in circumferential direction width from a relatively larger dimension at the distal end 30 to a relatively smaller dimension at the proximal limit of the axial slot 15. See FIG. 7. In the illustrated embodiment, each slot 15 has a width of about 0.20 inches at the proximal end and a width of about 0.035 inches at the distal end in the unstressed orientation. The width of the slot 15 may taper continuously throughout its length, or, as in the illustrated embodiment, is substantially constant for a proximal section and tapered over a distal section of the slot 15. The wall thickness of the lever arm 23 may also be tapered to increase the diameter of the central lumen 11 in the distal direction. This will allow a lower compressed crossing profile before the inside surfaces of the lever arms bottom out against each other.

Figure 12:
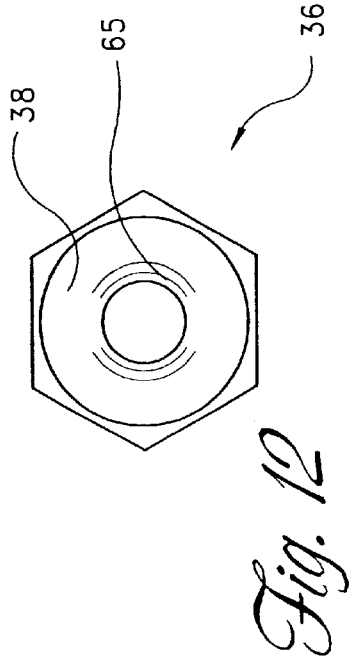
FIG. 12 is a proximal end elevational view of the proximal anchor end of FIG. 11.

The pin 26 is additionally provided with a plurality of retention structures 44 as has been discussed. Retention structures 44 are spaced apart axially along the pin 26 between a proximal limit 46 and a distal limit 48. The axial distance between proximal limit 46 and distal limit 48 is related to the desired axial travel of the proximal anchor 36, and thus the range of functional sizes of the pin. In one embodiment of the pin 26, the retention structures 44 comprise a plurality of threads, adapted to cooperate with the complimentary retention structures 42 on the proximal anchor 36, which may be a complimentary plurality of threads. In this embodiment, the proximal anchor 36 may be distally advanced along the pin 26 by rotation of the proximal anchor 36 with respect to the pin 26. Proximal anchor 36 may advantageously be removed from the pin 26 by reverse rotation, such as to permit removal of the pin 26 from the patient. For this purpose, collar 38 is preferably provided with a gripping configuration or structure to permit a removal tool to rotate collar 38 with respect to the pin 26. Any of a variety of gripping surfaces may be provided, such as one or more slots, flats, bores, or the like. In the illustrated embodiment, the collar 38 is provided with a polygonal, and in particular, a hexagonal circumference, as seen in FIG. 12.

The proximal end 28 of the pin 26 is similarly provided with a structure 29 for permitting rotational engagement with an installation or a removal tool. Rotational engagement may be accomplished using any of a variety of shapes or configurations, as will be apparent to those of skill in the art. One convenient structure is to provide the proximal end 26 with one or more flat side walls, for rotationally engaging a complimentary structure on the corresponding tool. As illustrated in FIG. 9, the proximal end 26 may be provided with a structure 29 having a square cross-section. Alternatively, the exterior cross-section through proximal end 28 may be any of a variety of configurations to permit rotational coupling, such as triangular, hexagonal, or other polygons, or one or more axially extending flat sides or channels on an otherwise round body.

The foregoing structures enable the use of an installation and/or deployment tool having a concentric core within a sleeve configuration in which a first component (e.g. a sleeve) engages the proximal anchor 36 and a second component (e.g. a core) engages the proximal rotational engagement structure 29 of pin 26. The first component may be rotated with respect to the second component, so that the proximal anchor 36 may be rotated onto or off of the retention structures 44 on pin 26. In a modified arrangement, a first tool (e.g., a pair of pliers or a wrench) may be used to engage the proximal anchor 36 and a second tool (e.g., a pair of pliers or a wrench) may be used to engage the proximal rotational engagement structure 29 of pin 26. In such an arrangement, the first tool may be rotated with respect to the second tool (or vice versa), so that the proximal anchor 36 may be rotated onto or off the retention structures 44 on the pin 26.

Alternatively, the retention structures 42 on the proximal anchor 36 may be toleranced to permit distal axial advancement onto the pin 26, such as by elastic deformation, but require rotation with respect to the pin 26 in order to remove the proximal anchor 36 from the pin 26.

Any of a variety of alternative retention structures may be configured, to permit removal of the proximal anchor 36 such as following implantation and a bone healing period of time. For example, the retention structures 44 such as threads on the pin 26 may be provided with a plurality of axially extending flats or interruptions, which correspond with a plurality of axial flats on the retention structures 42 of proximal anchor 36. This configuration enables a partial rotation (e.g. 90°) of the proximal anchor 36 with respect to the pin 26, to disengage the corresponding retention structures and permit axial withdrawal of the proximal anchor 36 from the pin 26. One or both of the retention structures 44 and 42 may comprise a helical thread or one or more circumferentially extending ridges or grooves. In a threaded embodiment, the thread may have either a fine pitch or a course pitch. A fine pitch may be selected where a number of rotations of proximal anchor 36 is desired to produce a relatively small axial travel of the anchor 36 with respect to the pin 26. In this configuration, relatively high compressive force may be achieved between the proximal anchor 36 and the distal anchor 34. This configuration will also enable a relatively high resistance to inadvertent reverse rotation of the proximal anchor 36. Alternatively, a relatively course pitch thread such as might be found on a luer connector may be desired for a quick twist connection. In this configuration, a relatively low number of rotations or partial rotation of the proximal anchor 36 will provide a significant axial travel with respect to the pin 26. This configuration may enhance the tactile feedback with respect to the degree of compression placed upon the bone. The thread pitch or other characteristics of the corresponding retention structures can be optimized through routine experimentation by those of skill in art in view of the disclosure herein, taking into account the desired clinical performance.

Referring to FIG. 7, at least a first break point 31 may be provided to facilitate breaking the proximal portion of the pin 26 which projects proximally of the collar 38 following tensioning of the fixation system. Break point 31 in the illustrated embodiment comprises an annular recess or groove, which provides a designed failure point if lateral force is applied to the proximal end 28 while the remainder of the attachment system is relatively securely fixed. At least a second break point 33 may also be provided, depending upon the axial range of travel of the proximal anchor 36 with respect to the pin 26.

In one embodiment having two or more break points 31, 33, the distal break point 31 is provided with one or more perforations or a deeper recess than the proximal break point 33. In this manner, the distal break point 31 will preferentially fail before the proximal break point 33 in response to lateral pressure on the proximal end 28. This will ensure the minimum projection of the pin 26 beyond the collar 38 following deployment and severing of the proximal end 28 as will be appreciated in view of the disclosure herein.

Figure 11:
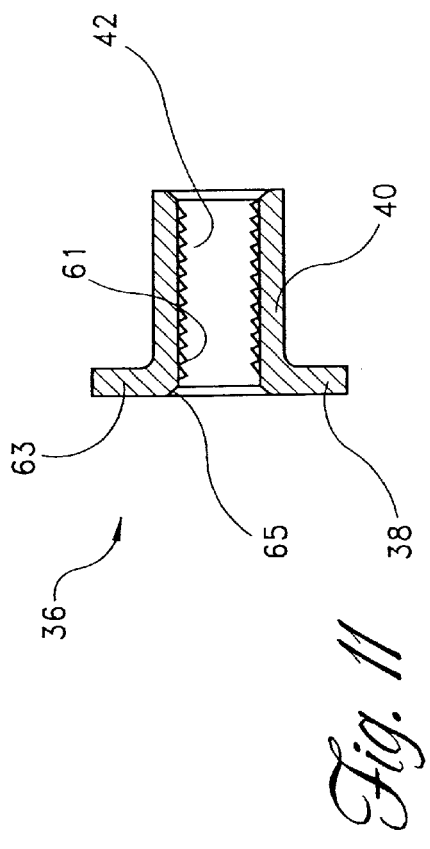
FIG. 11 is a cross-sectional view through a proximal anchor for use with the pin body of FIG. 7.

Proximal projection of the proximal end 28 from the proximal anchor 36 following implantation and breaking at a breakpoint 31 may additionally be minimized or eliminated by allowing the breakpoint 31 or 33 to break off within the proximal anchor 36. Referring to FIG. 11, the retention structure 42 may terminate at a point 61 distal to a proximal surface 63 on the anchor 36. An inclined or tapered annular surface 65 increases the inside diameter of the central aperture through proximal anchor 36, in the proximal direction. After the proximal anchor 36 has been distally advanced over a pin 26, such that a breakpoint 31 is positioned between the proximal limit 61 and the proximal surface 63, lateral pressure on the proximal end 28 of pin 26 will allow the breakpoint 31 to break within the area of the inclined surface 65. In this manner, the proximal end of the pin 26 following breaking resides at or distally of the proximal surface 63, thus minimizing the profile of the device and potential tissue irritation.

For any of the (axially deployable) embodiments disclosed above, installation can be simplified through the use of an installation tool. The installation tool may comprise a pistol grip or plier-type grip so that the clinician can position the tool at the proximal extension of pin 32 and through one or more contractions with the hand, the proximal anchor 36, 52 and distal anchor 34 can be drawn together to appropriately tension against the bone fragments. The use of a precalibrated tool can permit the application of a predetermined tension in a uniform manner from pin to pin.

Calibration of the installation device to set a predetermined load on the pin can be accomplished through any of a variety of means which will be understood to those of skill in the art. For example, the pin 32 may be provided with one or more score lines or transverse bores or other modifications which limit the tensile strength of the part at one or more predetermined locations. In this manner, axial tension applied to the proximal end 28 with respect to the collar 54 will apply a predetermined load to the bone before the pin 32 will separate at the score line. Alternatively, internal structures within the installation tool can be provided to apply tension up to a predetermined limit and then release tension from the distal end of the tool.

Figure 13:
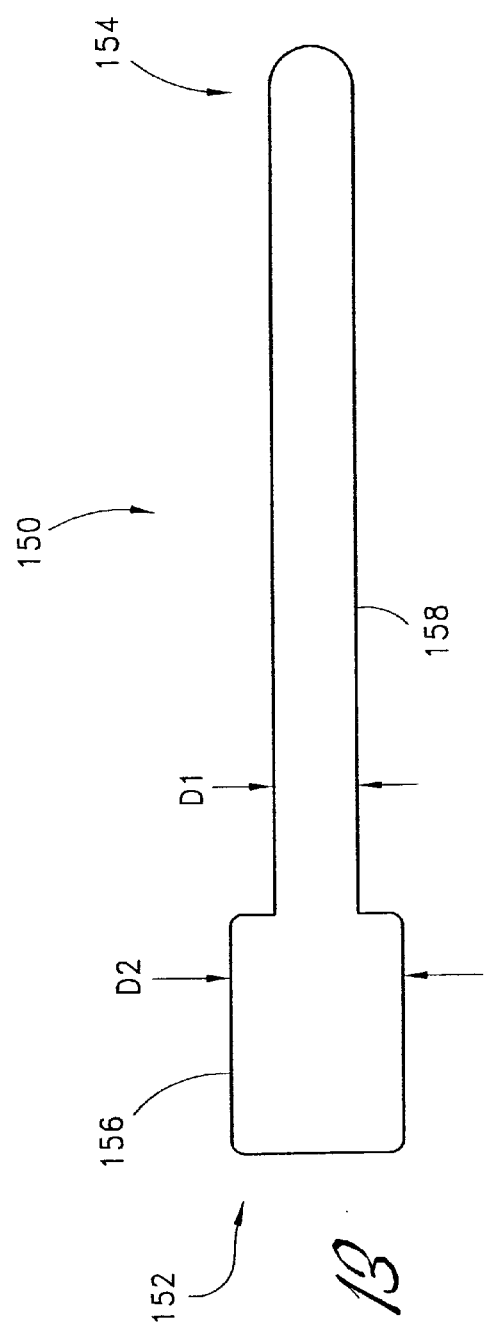
FIG. 13 is a side elevational view of a guide wire that may be used with the pin body of FIG. 7.

FIGS. 13 illustrates a locking guide wire 150 that may be used with the fixation device described above. The guide wire has a distal end 152 and a proximal end 154. The illustrated guide wire 150 comprises a locking portion 156 that is located at the distal end 152 of the guide wire 150 and an elongated portion 158 that preferably extends from the distal portion 156 to the proximal end 154 of the guide wire 150. The diameter D1 of the elongated portion 158 is generally smaller than the diameter D2 of the distal portion 154. The guide wire 150 can be made from stainless steel, titanium, or any other suitable material. Preferably, in all metal systems, the guidewire 150 and locking portion 156 are made from the same material as the remainder of the fixation device to prevent cathodic reactions.

The locking portion 156 on guidewire 150 can take any of a variety of forms, and accomplish the intended function as will be apparent to those of skill in the art in view of the disclosure herein. For example, a generally cylindrical locking structure, as illustrated, may be used. Alternatively, any of a variety of other configurations in which the cross section is greater than the cross section of the proximal portion 158 may be used. Conical, spherical, or other shapes may be utilized, depending upon the degree of compression desired and the manner in which the locking portion 156 is designed to interfit with the distal end 30 of the pin.

The guide wire 150 is configured such that its proximal end can be threaded through the lumen 11 of the pin 26. With reference to FIG. 8, the lumen 11 preferably comprises a first portion 160 and a second portion 162. The first portion 160 is generally located at the distal end 30 within the region of the lever arms of the pin 26. The second portion 162 preferably extends from the first portion 160 to the proximal end 28 of the pin 26. The inside diameter of the first portion 160 is generally larger than the diameter of the second portion 162. As such, the junction between the first portion 160 and the second portion 162 forms a transverse annular engagement surface 164, which lies transverse to the longitudinal axis of the pin 26.

As mentioned above, the guide wire 150 is configured such that its proximal end can be threaded through the lumen 11 of the pin 26. As such, the diameter D1 of the elongated portion 158 is less than the diameter of the second portion 162 of the lumen 11. In contrast, the diameter D2 of distal portion 156 preferably is slightly smaller than equal to or larger than the diameter of the first portion 160 and larger than the diameter of the second portion 162. This arrangement allows the distal portion 156 to be retracted proximally into the first portion 160 but prevents the distal portion 156 from passing proximally through the pin 26.

In addition, any of a variety of friction enhancing surfaces or surface structures may be provided, to resist distal migration of the locking guidewire 150, post deployment. For example, any of a variety of radially inwardly or radially outwardly directed surface structures may be provided along the length of the locking guidewire 150, to cooperate with a corresponding surface structure on the inside surface of the lumen 11, to removably retain the locking guidewire 150 therein. In one embodiment, a cylindrical groove is provided on the inside surface of the lumen 11 to cooperate with a radially outwardly extending annular flange or ridge on the outside diameter of the locking guidewire 150. The complementary surface structures may be toleranced such that the locking guidewire or guide pin may be proximally retracted into the lumen 11 to engage the locking structure, but the locking structure provides a sufficient resistance to distal migration of the locking guidewire 150 such that it is unlikely or impossible to become disengaged under normal use.

In use, after the clinician assesses the bone, selects a bone drill and drills a through hole 22, the distal end 152 of the guide wire 150 and the distal end 30 of the pin 26 are advanced through the through hole until the distal portion 156 and the barbs 50 exit the distal aperture 20. The proximal anchor 36 may be positioned on the bone fixation device 24 prior to positioning of the pin body 32 in the through hole 22, or following placement of the pin body 32 within through hole 22.

Figure 14:
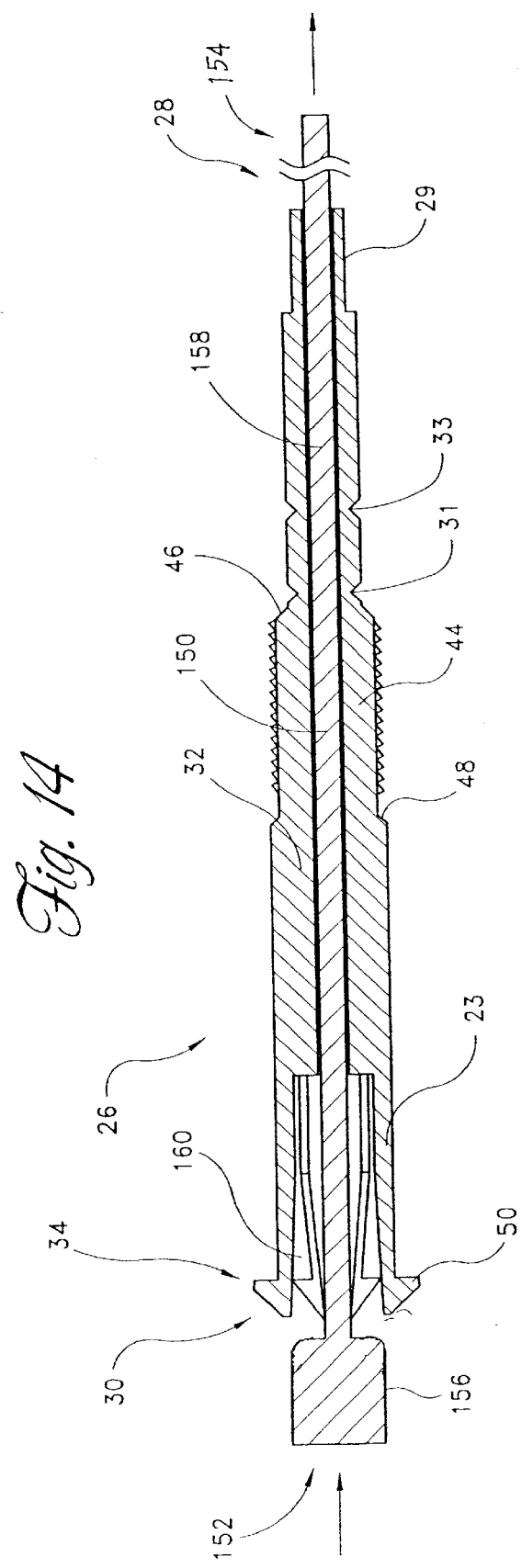
FIG. 14 is a longitudinal cross-sectional view of the guide wire of FIG. 13 and the pin body of FIG. 7.

The guide wire 150 is preferably thereafter retracted until the distal portion 156 enters, at least partially, the first portion 160 of the pin 26 (see FIG. 14). The proximal anchor 36 can then be rotated or otherwise distally advanced with respect to the pin body 26 so as to seat the distal anchor 34 snugly against the distal component 21 of the bone. As such, at least a part of the distal portion 156 of the guide wire 150 becomes locked within the first portion 150 of the pin 26. This prevents the barbs 50 and lever arms 24 from being compressed radially inward and ensures that the barbs 50 remain seated snugly against the distal component 21 of the bone.

Following appropriate tensioning of the proximal anchor 36, the proximal end 28 of the pin body 32 and the proximal end 154 of the guide wire 150 are preferably cut off or otherwise removed. These components may be cut using conventional bone forceps which are routinely available in the clinical setting, or snapped off using designed break points as has been discussed.

The specific dimensions of any of the bone fixation devices of the present invention can be readily varied depending upon the intended application, as will be apparent to those of skill in the art in view of the disclosure herein. In addition, although the present invention was disclosed in the context of a cortical to cortical compression fixation which uses a through hole, the invention may be readily dimensioned to suit non-through hole applications. Features from the various embodiments described above may also be incorporated into the other.

Although the present invention has been described in terms of certain preferred embodiments, other embodiments of the invention including variations in dimensions, configuration and materials will be apparent to those of skill in the art in view of the disclosure herein. In addition, all features discussed in connection with any one embodiment herein can be readily adapted for use in other embodiments herein. The use of different terms or reference numerals for similar features in different embodiments does not imply differences other than those which may be expressly set forth. Accordingly, the present invention is intended to be described solely by reference to the appended claims, and not limited to the preferred embodiments disclosed herein.

What is claimed is:

1. A fixation pin for fixing bone to bone or other tissue to bone, comprising:
    A tubular body, having a proximal end and a distal end;
    At least two slots in the tubular body, extending proximally from the distal end to define at least a first and a second axially extending lever arms;
    A proximally facing retention surface carried by each lever arm;
    A thread on the body, proximal to the lever arms, for removably carrying a proximal anchor; and
    A proximal anchor carried by the body, comprising an aperture for receiving the tubular body and a collar for seating against a tissue surface;
    Wherein the first and second retention surfaces are laterally movable between an implantation crossing profile and a deployed crossing profile.

2. A fixation pin as in claim 1, wherein rotation of the proximal anchor with respect to the tubular body moves the proximal anchor axially along the tubular body.

3. A fixation pin as in claim 1, wherein the tubular body includes a bore that extends longitudinally through the tubular body from the proximal end to the distal end, the bore having a first portion at the distal end and a second portion located adjacent to the first portion, the second portion having a diameter that is smaller than the first portion.

4. A fixation pin as in claim 3, further including a guide wire that extends through the bore and includes a distal portion configured to fit within the first portion so as to keep said first and second retention surfaces from laterally moving from the deployed crossing profile.

5. A fixation pin as in claim 3, further comprising a guide wire configured to be inserted into the bore, the bore and the guide wire having complementary surface structures that prevent distal migration of the guidewire under normal use.

6. Fixation pin as in claim 1, wherein the first and second retention surface are biased in the direction of the deployed crossing profile.

7. A fixation pin as in claim 1, further comprising a third slot in the tubular body, extending proximally from the distal end to define, in part, a third axially extending lever arm.

8. A fixation pin as in claim 1, wherein all elements except the proximal anchor are integrally formed from a single piece of metal.

9. A fixation pin as in claim 8, wherein the metal comprises titanium.

10. A fixation pin as in claim 1, further comprising a break point on the body.

11. A fixation pin as in claim 1, further comprising a rotational coupling on the body, for removably rotationally coupling the body to a tool.

12. A fixation pin as in claim 1, wherein the tubular body has an axial length within the range of from about 5 mm to about 70 mm.

13. A fixation pin as in claim 1, wherein the tubular body has a diameter within the range of from about 1.5 mm to about 7 mm.

14. A method of fixing a first material to bone, comprising the steps of:
    Providing a pin having a distal anchor and at least one proximal break point;
    Advancing the distal anchor through the first material and into the bone;
    Advancing a distal end of a guide wire through the first material and into the bone and retracting the distal end of the guide wire into a distal portion of a bore that extends longitudinally through the pin;

Advancing a proximal anchor distally along the pin to secure the first material to the bone; and Applying lateral pressure on a proximal portion of the pin to break the pin at the break point.

15. A method of fixing a first material to bone as in claim 14, wherein the first material comprises bone.

16. A method of fixing a first material to bone as in claim 14, wherein the first material comprises soft tissue.

17. A method of fixing a first material to bone as in claim 14, wherein the advancing the distal anchor step comprises advancing the distal anchor all the way through the bone.

18. A method of fixing a first material to bone as in claim 17, wherein the advancing proximal anchor step comprises rotating the proximal anchor with respect to the pin.

19. A method of fixing a first material to bone as in claim 18, further comprising the step of removing the proximal anchor by rotating the proximal anchor with respect to the pin.

20. A method of fixing a first material to bone as in claim 14, wherein the advancing a proximal anchor step comprises rotating the proximal anchor with respect to the pin.

21. A method of fixing a first material to bone as in claim 20, further comprising the step of removing the proximal anchor by rotating the proximal anchor with respect to the pin.

22. A method of fixing a first material to bone as in claim 14, further comprising the step of removing the proximal anchor by rotating the proximal anchor with respect to the pin.

23. A method of fixing a first material to bone as in claim 14, wherein the pin has an axial length within the range of from about 5 mm to about 70 mm.

24. A method of fixing a first material to bone as in claim 14, wherein the pin has a diameter within the range of from about 1.5 mm to about 7 mm.

25. A method of fixing a first material to a bone as in claim 14, wherein the step of advancing the distal anchor through the first material and into the bone comprises advancing the distal anchor through a bone of a hand.

26. A method of fixing a first material to a bone as in claim 14, wherein the step of advancing the distal anchor through the first material and into the bone comprises advancing the distal anchor through a bone of a leg.

27. A fixation pin for fixing a first material to bone, comprising:

An elongate tubular body, having a proximal end and a distal end;

A plurality of deflectable barbs carried by the distal end;

A thread on the tubular body, in between the proximal end and the distal end;

A break point on the tubular body, proximal to at least a portion of the thread; and A rotational coupling on the pin, for coupling to a tool.

28. A fixation pin as in claim 27, further comprising a proximal anchor, removably retained on the tubular body by the thread.

29. A fixation pin as in claim 27, wherein each of the barbs is attached to the tubular body by an axially extending lever arm.

30. A fixation pin as in claim 27, wherein the body includes a bore that extends longitudinally through the body from the proximal end to the distal end, the bore having a first portion at the distal end and a second portion located adjacent the first portion, the second portion having a diameter smaller than the first portion.

31. A fixation pin as in claim 30, further including a guide wire that extends through the bore and includes a distal portion configured to fit within the first portion so as to keep said first and second retention surfaces from laterally moving from the second, larger deployed crossing profile.

32. A fixation pin as in claim 27, integrally formed from a single piece of metal.

33. A fixation pin as in claim 32, wherein the metal comprises titanium.

34. A fixation pin as in claim 27, wherein the tubular body has an axial length within the range of from about 5 mm to about 70 mm.

35. A fixation pin as in claim 27, wherein the tubular body has a diameter within the range of from about 1.5 mm to about 7 mm.

36. A fixation pin as in claim 27, wherein the tubular body is formed from a bioabsorbable material.

37. A fixation pin for fixing a first material to bone, comprising:

An elongate tubular body, having a proximal end and a distal end;

A plurality of deflectable barbs carried by the distal end;

A thread on the tubular body, in between the proximal end and the distal end;

A break point on the tubular body, proximal to at least a portion of the thread; and wherein the body includes a bore that extends longitudinally through the body from the proximal end to the distal end, the bore having a first portion at the distal end and a second portion located adjacent the first portion, the second portion having a diameter smaller than the first portion.

38. A fixation pin as in claim 37, further including a guide wire that extends through the bore and includes a distal portion configured to fit within the first portion so as to keep said first and second retention surfaces from laterally moving from the second, larger deployed crossing profile.

39. A fixation pin as in claim 38, further comprising complementary structures on the bore and the guide wire to prevent distal migration of the guide wire.

40. A fixation pin as in claim 37, further comprising a proximal anchor, removably retained on the tubular body by the thread.

41. A fixation pin as in claim 37, wherein each of the barbs is attached to the tubular body by an axially extending lever arm.

42. A fixation pin as in claim 37, integrally formed from a single piece of metal.

43. A fixation pin as in claim 37, wherein the metal comprises titanium.

44. A fixation pin as in claim 37, wherein the tubular body has an axial length within the range of from about 5 mm to about 70 mm.

45. A fixation pin as in claim 37, wherein the tubular body has a diameter within the range of from about 1.5 mm to about 7 mm.

46. A method of fixing a first piece of bone to a second piece of bone, comprising the steps of:

providing a pin having at least one laterally moveable distal anchor;

advancing the distal anchor through the first piece of bone and into the second piece of bone while the distal anchor is permitted to move radially inwardly as needed;

advancing a proximal anchor distally along the pin to secure the first piece of bone to the second piece of bone; and moving a wire axially through a lumen to resist radial inward deflection of the distal anchor, thereby locking the distal anchor and engaging the lumen to prevent distal migration of the wire.

47. A method of fixing a first piece of bone to a second piece of bone as in claim 46, wherein the advancing the distal anchor step comprises advancing the distal anchor all the way through the second piece of bone.

48. A method of fixing a first piece of bone to a second piece of bone as in claim 47, wherein the advancing a proximal anchor step comprises rotating the proximal anchor with respect to the pin.

49. A method of fixing a first piece of bone to a second piece of bone as in claim 48, further comprising the step of removing the proximal anchor by rotating the proximal anchor with respect to the pin.

50. A method of fixing a first piece of bone to a second piece of bone as in claim 46, wherein the advancing a proximal anchor step comprises rotating the proximal anchor with respect to the pin.

51. A method of fixing a first piece of bone to a second piece of bone as in claim 50, further comprising the step of removing the proximal anchor by rotating the proximal anchor with respect to the pin.

52. A method of fixing a first piece of bone to a second piece of bone as in claim 51, wherein the moving a wire step comprises proximally retracting a wire having a locking structure thereon.

53. A method of fixing a first piece of bone to a second piece of bone as in claim 46, further comprising the step of removing the proximal anchor by rotating the proximal anchor with respect to the pin.

54. A method of fixing a first piece of bone to a second piece of bone as in claim 53, wherein the moving a wire step comprises proximally retracting a wire having a locking structure thereon.

55. A method of fixing a first piece of bone to a second piece of bone as in claim 54, the distal anchor comprises at least three lever arms.

56. A method of fixing a first piece of bone to a second piece of bone as in claim 46, wherein the moving a wire step comprises proximally retracting a wire having a locking structure thereon.

57. A method of fixing a first piece of bone to a second piece of bone as in claim 56, wherein the distal anchor comprises at least three lever arms.

58. A method of fixing a first piece of bone to a second piece of bone as in claim 46, wherein the pin has an axial length within the range of from about 5 mm to about 70 mm.

59. A method of fixing a first piece of bone to a second piece of bone as in claim 46, wherein the pin has a diameter within the range of from about 1.5 mm to about 7 mm.

60. A method of fixing a first piece of bone to a second piece of bone as in claim 46, wherein the pin is formed from a bioabsorbable material.

* * * * *